United States Patent [19]

Pauly

[11] 4,419,343

[45] Dec. 6, 1983

[54] COMPOSITION USABLE NOTABLY AS A COSMETIC PRODUCT ALLOWING A TANNING OF THE SKIN COMPRISING THE USE OF AMINOACIDS

[75] Inventor: Marc Pauly, Chateau Salins, France

[73] Assignee: Laboratorios Serobiologiques S.A., France

[21] Appl. No.: 294,402

[22] Filed: Aug. 19, 1981

Related U.S. Application Data

[63] Continuation of Ser. No. 84,019, Oct. 12, 1979, abandoned.

[30] Foreign Application Priority Data

Oct. 19, 1978 [FR] France ................. 78 29797

[51] Int. Cl.$^3$ ............... C07C 143/00; A61K 7/42; C07D 233/64; C07C 83/00
[52] U.S. Cl. ................. 424/59; 260/501.11; 260/501.12; 424/60; 424/78; 424/168; 424/357; 548/344
[58] Field of Search ............ 424/59, 60; 548/344; 260/501.11, 501.12

[56] References Cited

U.S. PATENT DOCUMENTS 4,021,538  5/1977  Yu et al. ................. 424/60

FOREIGN PATENT DOCUMENTS

| 458709 | 10/1945 | Belgium | 424/59 |
| 823675 | 12/1973 | Belgium | 424/59 |
| 1003922 | 3/1957 | Fed. Rep. of Germany | 424/59 |
| 1252400 | 12/1960 | France | 424/59 |
| 43-7204997 | 4/1968 | Japan | 424/59 |

OTHER PUBLICATIONS

Sagarin, Cosmetics Science & Technology, 1957, pp. 190-201, 1113-1131.
Merck Index, p. 1262.
Janistyn, Handbuch der Kosmetika und Reichstoffe, Bd. I, 6/1973, pp. 1117-1119.
J. Soc. Cosm. Chemists, 1970, pp. 817-823.
J. of Am. Pharm. Assoc., 1950, Index to vol. 39, pp. 30 to 36.

*Primary Examiner*—Dale R. Ore
*Attorney, Agent, or Firm*—Steinberg & Raskin

[57] ABSTRACT

The invention relates to a composition promoting photo-pigmentation and/or photo-protection of the epidermis by exposure to sun or UV rays.

The composition comprises at least a natural substance homologous or analogous to those normally present in the epidermis, said homologous substance being constituted by an aminoacid or a derivative thereof acting, directly or indirectly, onto the melanogenesis.

This composition is usable notably as a cosmetic product under topical application onto the epidermis.

19 Claims, No Drawings

COMPOSITION USABLE NOTABLY AS A COSMETIC PRODUCT ALLOWING A TANNING OF THE SKIN COMPRISING THE USE OF AMINOACIDS

This is a continuation of application Ser. No. 84,019, filed Oct. 12, 1979, now abandoned.

The present invention essentially relates to a composition usable notably as a cosmetic product promoting the tanning of the skin.

More specifically, this invention relates to a composition, usable notably as a cosmetic product aimed to be applied topically onto the epidermis to promote its photo-pigmentation and/or its photo-protection during exposure to sun or ultraviolet rays.

Compositions are already known for promoting the tanning of the skin and/or its photo-protection. For instance, so called anti-sun preparations are known which allow exposure to sun, with tanning, while protecting the skin from UV B rays, which are well known to be erythematogen and dangerous, which use screen substances or sun filters prepared by synthesis such as salicylates, anthranilates, cinnamates or para-amino benzoic esters or natural substances obtained through extraction from plants, for instance, plant oils, sesame, camomile.

Other known preparations use *photo-sensibilizers* applied internally or topically, prepared by synthesis such as furocoumarines or 5 or 8-methoxypsoralene (M.O.P.), or from natural origin such as bergamot oil, vitamine A or F.

Also other so called tanning or *tanning without sun,* products are known which use chemical agents such as dihydroxyacetone, erythrulose, glycerose. In the same way other known preparations use coloring or tanning products which provide a brownish or tanned color or shade.

Nevertheless, all these known preparations or compositions permitting a tanning of the skin with or without sun use agents extraneous to the skin and present very important and well known *drawbacks.* Indeed, these extraneous agents are scarcely substantive. On the other hand, they are more or less well tolerated. Besides, they must be used in repeated and frequent applications due to the difficulty of their penetration within the external layers of the epidermis.

Some of these known preparations are even dangerous, particularly the photo-sensibilizers based preparations and must thus be used with caution.

The main object of the present invention is to remedy said drawbacks of the known tanning preparations or compositions by providing a solution which permit the realization of a photo-pigmentation of the epidermis and/or its photo-protection during exposure to sun or ultraviolet rays, which is well tolerated by the epidermis and avoids the formation of erythemes or sunburns which are painful and can have consequences more or less serious. This solution must preferably be of a particularly simple conception.

This solution consists, according to the present invention in a composition, usable notably as a cosmetic product, and dermo-corrective (case of achromies) aimed to be applied topically onto the epidermis to promote its photo-pigmentation and/or its photo-protection during exposure to sun or ultra-violet rays, characterized in that it comprises at least a natural substance homologous or analogous to those normally present in the epidermis, said homologous substance being an aminoacid or a derivative thereof acting, directly or indirectly, on the melanogenesis. It results therefrom that the invention composition is perfectly tolerated by the patient.

Besides, it must be noted that the photo-protective or pigmentogene properties of the invention composition are only spread out on the contact of the epidermis itself, and only after photo-incitment by sun or ultra-violet rays (either UV A alone, or UV A+UV B). It results therefrom that the invention composition permits to reinforce and accelerate the *natural* process of pigmentation, or melanogenesis of the skin by exposure to the sun or UV rays. Another advantage resides in the fact that it speeds up the *self-photoprotection* process of the skin against the ultra-violet rays well known as dangerous (UV B), this self-protection being correlated to the intensity or strength of the pigmentation and other cutaneous factors.

Also achieved, unexpectedly, is a complementary photo-protection against the dangerous effects of sun exposures savage or excessive in intensity or strength or duration, notably for patients who are not prepared thereon, and permitting the protection of said patients against the consequences of repeated sun exposures causing a precocious aging of the skin, or promoting cutaneous cancers.

The invention composition also permits the lessening of the painful effects due to the consequences of excessive sun exposures, which cause painful erythemes or sunburns and which can provide consequences more or less serious for the patient.

Another very important advantage of the invention composition resides in the fact that it can be used for the medical treatment of achromic anomalies of the skin, such as leucodermies, partial albinism, vitiligo by restoring a normal pigmentation of the skin. The invention composition is indeed particularly adapted to these medical applications due to the fact that, as previously emphasized, it uses only natural substances normally residing in the epidermis and that it presents therefore a perfect tolerance and innocuousness, said natural substances being easily used by the epidermis, even partially, to reinforce the activity or intensity of the natural processes of photo-pigmentation and self-protection of the skin in response to the sun or UV irradiations.

As homologous substances acting, directly or indirectly to the melanogenesis, can be used preferably, according to the present invention a melanine precursor and, advantageously, this melanine precursor is constituted by tyrosine, and preferably L-tyrosine.

According to a particularly advantageous feature of the present invention, tyrosine is combined with an inorganic base and preferably with an organic base to form a complex salt presenting a better diffusibility in the epidermis.

As inorganic bases, can be cited by way of example soda, potash, magnesium or aluminium hydroxide, ammoniated bases such as $NH_4OH$, $NH_3$. As organic bases, which are preferred according to the invention, can be used by way of example ethanol-amine, diethanolamine, triethanolamine. Most preferably, said tyrosine complex salt is formed by combining tyrosine with at least one basic aminoacid, this basic amino-acid being advantageously selected from arginine, ornithine, citrulline, lysine or hydroxylysine.

According to another advantageous feature of the invention, the composition comprises, besides said melanine precursor, from about 0.1 to about 1% of tyrosinase.

According to another advantageous feature of the invention, the composition comprises, besides said melanine precursor, at least one homologous substance selected from the group consisting of:

(a) usual aminoacids such as:
mono-carboxylic monoamines, preferably:
α and β amino propionic acids, valine, leucine, isoleucine, at a concentration ranging between 0.1 and 10 weight % with respect to the composition;
hydroxylated aminated acids, preferably:
serine, threonine at a concentration ranging between 0.01 and 10 weight % with respect to the composition;
dicarboxylic mono-aminated acids, preferably:
aspartic acid at a concentration ranging between 0.01 and 10 weight % with respect to the composition,
glutamic acid at a concentration ranging between 0.01 to 15 weight % with respect to the composition;
aromatic or cyclic aminated acids, preferably:

| (weight percent with respect to the composition) | |
|---|---|
| proline | 0.010 to 5 |
| hydroxyproline | 0.01 to 5 |
| histidine | 0.01 to 15 |
| tryptophane | 0.01 to 15 | monocarboxylic aminated acids with several amino functions, preferably:
ornithine, citrulline, lysine, hydroxylysine, at a concentration ranging between 0.1 and 10 weight % with respect to the composition;

(b) cyto-protective aminoacids such as amino sulfurated acids, preferably glutathion, cystine, cysteine, or methionine at a concentration ranging between 0.01 and 15 weight % with respect to the composition;

(c) natural photo-protective aminoacids, or derivatives thereof, preferably urocanic acids and the salts thereof at a concentration ranging between 0.1 and 10 weight % with respect to the composition, so that the total concentration in homologous substances ranges between 0.1 and 20 weight % with respect to the composition.

It can be noted that the association and the combination of these homologous substances, which are cutaneo-constitutive of the epidermis, have a complementary or synergistic action as well as for the photo-pigmentation of the epidermis as for its photo-protection, i.e. that the association or combination of these substances permits not only reinforcement of the activity of each of them, but permits further a better compatibility with the epidermis, a better substantivity, solubility, diffusibility, penetrability and fixation in the epidermis.

It results therefrom that another advantage of the invention composition resides in its ease of use, mainly in topical use (external application), either in the solubilized, dispersed or diluted form with usual excipients or vehicles appropriate to this type of application, as well in cosmetic, hygienic products as dermatologic products, notably for the treatment of achromic anomalies of the skin (leucodermies, partial albinism, vitiligo).

The invention will be better understood and further objects, characterizing features, details and advantages thereof will appear more clearly as the following explanatory description proceeds with reference to the following examples given only for illustrative purposes, said examples not restricting therefore the scope of the present invention.

EXAMPLE 1

A composition is prepared comprising as melanine precursor, homologous substance, tyrosine, preferably L-tyrosine, in the form of a tyrosine-arginine base complex which is perfectly soluble and stable and the pH of which can be adjusted to neutrality or to the epidermis pH by varying the ratios of each of the constituents.

For instance, this complex is formed from 47% of tyrosine and from 53% of arginine base.

This complex is then diluted with one excipient or vehicle such as a hydric, hydroglycolic, hydroalcoholic excipient or vehicle, an oil/water or water/oil emulsion, a polymer gel, a varied or telluric organic gel: bentonites, clays, bentones, hectorites, cellulosic gels, so that this complex constitutes from 0.1 to 20% weight % of the total composition, this permitting the preparation of a composition usable notably in cosmetology and in sun products: photo-protectives, tanning products having different presentations.

EXAMPLE 2

A composition is prepared comprising as homologous substances the following constituents:

| | |
|---|---|
| arginine base | 52.9 |
| tyrosine | 47 |
| glutathion | 0.1 |

The preparation of this composition is realized as follows: first tyrosine and arginine base are mixed so as to realize a tyrosine-arginine complex and then is added glutathion. Thereafter, the association of these three components is diluted with a usual excipient or vehicle of the type defined in Example 1 hereabove so as to obtain a composition having a total concentration in aminoacids ranging between 0.1 and 20 weight % of the composition.

It must be noted that this association arginine-tyrosine-glutathion has a particularly important cellular photo-protective effect. As a matter of fact, glutathion has a moderating protective effect against the cellular damages induced by quinones, which are intermediaries highly reactive, which interfere in the melanogenesis process, these quinones being known to adversely affect the RNA of the epidermic cells.

It must be also noted that glutathion can be replaced by other sulfurated aminoacids such as cystine, cysteine, methionine.

EXAMPLE 3

A composition is prepared comprising as homologous substances the following constituents:

| | |
|---|---|
| arginine base | 42 |
| tyrosine | 40 |
| glutathion | 0.1 |
| glycine | 17.9 |

This composition is prepared by forming first the tyrosine-arginine complex and then by adding thereto glutathion and glycine. Thereafter, this mixture is diluted within an excipient or vehicle so that the total concentration in homologous substances ranges between about 0.1 to about 20 weight %, said excipient or vehicle being one of those recited in Example 1.

It can be noted that glycine is a synergistic agent acting as a fixer or binder of the quinonic derivatives and of DOPA, which enter in the cycle of melanogenesis. This association thus reinforces or strengthens the cellular protective activity (RNA) and besides, is particularly substantive.

EXAMPLE 4

A composition is prepared comprising, as homologous substances, the following constituents:

| | |
|---|---|
| tyrosine | 38 |
| ornithine | 40 |
| glutathion | 0.1 |
| glycine | 17 |
| histidine | 4.9 |

The preparation of the composition is realized in the same way as that of the above Examples so as to obtain a total concentration in homologous substances ranging between 0.1 and 20 weight % of the composition.

It must be noted that histidine reinforces or strengthens the substantive action of the composition as well as its photo-protective effect due to the fact that histidine is the precursor of urocanic acid present in the epidermis and the sweat glands or sudoriparus glands.

Thus, histidine can be replaced for urocanic acid or the derivatives thereof, particularly arginine urocanate, histidine urocanate, or arginine-histidine urocanate.

It must also be noted that urocanic acid constitutes the natural photo-protector, the most functional for the skin, by partially hindering or stopping the ultra-violets B which are nocive. On the other hand, free urocanic acid being little soluble and little substantive, the salts thereof, and particularly the salts thereof with aminoacids, present the great advantage of being soluble, active as concerns photo-protectibility and substantivity on the epidermis.

EXAMPLE 5

A composition is prepared providing excellent results having a total concentration in homologous substances equal to 3% under the form of hydroglycerinated solute comprising the following constituents:

| | |
|---|---|
| complex tyrosine-arginine (47/53) | 0.25 |
| histidine | 0.03 |
| arginine urocanate | 0.15 |
| glycine | 2.52 |
| glutathion | 0.05 |
| glycerine | 20 |
| water | QS to 100 |

EXAMPLE 6

A composition is prepared comprising the following constituents (homologous substances=3 weight %)

| | |
|---|---|
| L-tyrosine | 0.12 |
| L-arginine | 0.12 |
| glutathion | 0.01 |
| urocanic acid | 0.15 |
| L-arginine | 0.05 |
| tyrosinase | 0.1 |
| histidine | 0.03 |
| glycine | 2.42 |

| | |
|---|---|
| emulsionated excipient or vehicle | 97 |

EXAMPLE 7

A composition is prepared having a total concentration in homologous substances equal to 9%, with the following substituents:

| | |
|---|---|
| L-tyrosine | 1.00 |
| L-arginine | 0.50 |
| ornithine | |
| or citrulline | |
| or lysine | 0.50 |
| urocanic acid | 1.00 |
| L-arginine | 0.50 |
| lysine | 0.40 |
| histidine | 2.10 |
| glycine | 3.00 |
| emulsionated excipient | QS to 100 |

EXAMPLE 8

A composition is prepared forming a sun protective preparation having a total concentration in homologous substances equal to 3% of the composition, comprising the following constituents:

| | |
|---|---|
| tyrosine-arginine complex | 0.25 |
| arginine urocanate | 0.20 |
| histidine | 0.03 |
| glycine | 2.51 |
| glutathion | 0.01 |
| excipient | 97 |
| The excipient is constituted by the following components: | |
| glyceryl monostearate | 14 |
| lanoline derivative | 5 |
| diethylsebacate | 10 |
| isopropylmyristate | 15 |
| titane dioxide | 2 |
| glycerine | 6 |
| water | 45 |

As well as mineral quantities of preserving agents.

It must be noted that in the above formulations given merely by way of example, the excipient is only a vehicle, cosmetically or dermatologically adapted, without noticeable influence on the activity of the complexes or associations of the homologous substances according to the present invention.

In certain particular cases, the photo-protection can be reinforced by adding thereto synthesis sun filters such as cinnamates in quantities ranging between 0.1 and 5 weight % of the composition or further there can be added tanning reinforcers or strengtheners without sun such as D.H.A. (dihydroxyacetone) at a concentration ranging between 0.3 and 5 weight % of the composition.

To demonstrate the physiological actions of the invention composition, clinical tests have been carried out on patients suffering from achromies of the skin. The treated patients suffered of vitiligo.

To treat these patients, a topical preparation of the invention composition containing tyrosine was prepared, comprising a twenty percent propyleneglycol hydroglycolic solute wherein was dissolved at a content of 3% the following combination of homologous substances:

| | |
|---|---|
| arginine base | 4.5 |
| tyrosine | 4.0 |
| urocanic acid | 5.0 |
| histidine HCl | 0.1 |
| glutathion | 0.02 |
| glutamic acid | 86.38 |
| TOTAL | 100.00 |

For the treatment of vitiligo, topical applications of the above said composition were carried out each 24 hours onto the apigmented or irregularly pigmented areas, and thereafter irradiations were performed during a period of time of about 10 minutes-30 minutes with an UVR lamp of 250 watts. The UV rays emission comprises about: 20% UVB rays and 80% UVA rays.

Five patients suffering from vitiligo were treated with the above pharmaceutical composition by performing six successive irradiations of twenty minutes, each spaced from 24 hours, with the above UVR lamp.

The results were surprising as early as the first irradiation, by marginal repigmentation of the apigmented areas.

After the second irradiation, the repigmentation appears on the whole surface of the treated depigmented areas.

During the remaining irradiations, the repigmentation increases in strength, without appearance of erythemes.

These results are particularly unexpected since it has been hitherto difficult to find an effective treatment of vitiligo. The invention composition through topical applications allows the solving of such problem with a mere UV irradiation during a short period of time which clearly emphasizes the photo-pigmentogene activity of the invention composition under UVA-UVB exposure.

On the other hand, tests of toxicity have been carried out on mice by studying the primary cutaneous irritation according to the official method of analysis of cosmetics and beauty products established in the French Official Journal of Apr. 21, 1971. Also, a study has been carried out as concerns the index of primary occular irritation of mice together with of the superficial cutaneous aggressivity of the invention composition through iterative applications.

In each of the three above studies, carried out according to official procedures with the same composition as that used for the above-said treatment of vitiligo, no irritating effect was observed so that it can be concluded that the invention composition has no toxic effect.

Of course, the invention is by no means limited to the forms of embodiment described and illustrated, which have been given by way of example only. In particular, it comprises all means constituting technical equivalents to the means described as well as their combinations should the latter be carried out according to its gist and used within the scope of the following claims.

What is claimed is:

1. A composition for topical application to the epidermis to effect photo-pigmentation or photo-protection of skin upon exposure to the sun or ultra-violet rays, said composition comprising a skin photo-pigmentation or photo-protection effective amount of a salt of tyrosine with a basic aminoacid, distributed in a vehicle for topical application.

2. The composition according to claim 1, wherein the tyrosine concentration ranges between from about 0.1 and about 10 weight % of the composition.

3. Composition according to claim 1, wherein said basic aminoacid combined with tyrosine is arginine.

4. Composition according to claim 1, wherein said tyrosine is L-tyrosine.

5. A composition for topical application to the epidermis to effect photo-pigmentation or photo-protection of skin upon exposure to the sun or ultraviolet rays, said composition comprising a skin photo-pigmentation or photo-protection effective amount of a salt of L-tyrosine with a basic amino acid selected from the group consisting of arginine, ornithine, citrulline, lysine, hydroxylysine and histidine distributed in a vehicle for topical application.

6. The composition according to claim 5, and including about 0.1 to about 1 weight % of tyrosinase.

7. The composition according to claim 5, and including at least one substance selected from the group consisting of:
    (a) mono-carboxylic mono-amines, at a concentration ranging between 0.1 and 10 weight % with respect to the composition;
    amino-hydroxylated acids, at a concentration ranging between 0.01 and 10 weight % with respect to the composition;
    di-carboxylic mono-aminated acids,
    aromatic or cyclic aminated acids,
    mono-carboxylic aminated acids having several amino functions, at a concentration between 0.01 and 10 weight % with respect to the composition;
    (b) cyto-protective aminoacids at a concentration ranging between 0.01 and 15 weight % with respect to the composition;
    (c) natural photo-protective aminoacids, or the derivatives thereof at the concentration ranging between 0.1 and 10 weight % with respect to the composition so that the total concentration of said substances ranges between 0.1 and 20 weight % of the composition.

8. The composition of claim 7, wherein said cytoprotective aminoacid is urocanic acid used in the form of a complex derivative with one or more basic amino acids.

9. Composition according to claim 7, wherein said mono-carboxylic mono-amine is selected from the group consisting of α - and β-amino-propionic acids, valine, leucine and isoleucine.

10. Composition according to claim 1, wherein said amino-hydroxylated acid is selected from the group consisting of serine and threonine.

11. Composition according to claim 10 wherein said di-carboxylic mono-aminated acid is selected from the group consisting of aspartic acid present in a concentration of 0.01 to 10 weight % with respect to the composition, and glutamic acid in a concentration of 0.01 to 15 weight % with respect to the composition.

12. Composition according to claim 11, wherein said aromatic or cyclic aminated acid is selected from the group consisting of proline in an amount of 0.10 to 15 weight % of the composition, hydroxyproline in an amount of 0.01 to 5 weight % of the composition, histidine in an amount of 0.01 to 15 weight % of the composition and tryptophane in an amount of 0.01 to 15 weight % of the composition.

13. Composition according to claim 12, wherein said monocarboxylic aminated acid having several amino functions is selected from the group consisting of ornithine, citrulline, lysine, and hydroxylysine in a concentration of 0.01 to 10 weight % of the composition.

14. Composition according to claim 13, wherein said cyto-protective aminoacid is a sulfurated aminoacid.

15. Composition according to claim 14, wherein said sulfurated aminoacid is selected from the group consisting of glutathion, cystine, cysteine and methionine.

16. Composition according to claim 15, wherein said natural photo-protective aminoacid or derivative thereof is selected from the group consisting of urocanic acid and salts thereof.

17. Composition according to claim 8, wherein said basic aminoacid of said urocanic acid complex derivative is selected from the group consisting of histidine, arginine and mixtures thereof.

18. Method of promoting photo-pigmentation or photo-protection of the skin upon exposure to ultraviolet rays which comprises topically applying to the skin a photo-pigmentation or photo-protection effective amount of a salt of tyrosine with a basic aminoacid.

19. Method according to claim 18 wherein said basic aminoacid is selected from the group consisting of arginine, ornithine, citrulline, lysine, hydroxylysine and histidine.

* * * * *